United States Patent [19]

King

[11] Patent Number: 4,603,139
[45] Date of Patent: Jul. 29, 1986

[54] BICYCLE COMPOUNDS, PROCESSES FOR THEIR PREPARATION AND PHARMACEUTICAL FORMULATIONS CONTAINING COMPOUNDS

[75] Inventor: William R. King, Bickley, England

[73] Assignee: Burroughs Wellcome Co.

[21] Appl. No.: 690,815

[22] Filed: Jan. 11, 1985

Related U.S. Application Data

[60] Continuation of Ser. No. 522,995, Aug. 15, 1983, abandoned, which is a division of Ser. No. 440,258, Nov. 9, 1982, abandoned.

[30] Foreign Application Priority Data

Nov. 10, 1981 [GB] United Kingdom ............... 8133930
Nov. 10, 1981 [GB] United Kingdom ............... 8133942
May 12, 1982 [GB] United Kingdom ............... 8133846

[51] Int. Cl.$^4$ ............................................. A61K 31/44
[52] U.S. Cl. ............................................. 514/337
[58] Field of Search ........................ 424/213; 514/337

[56] References Cited

U.S. PATENT DOCUMENTS 3,985,891 10/1976 Kutter et al. ................... 424/263
4,281,005 7/1981 Baldwin .......................... 424/263

FOREIGN PATENT DOCUMENTS 820316 8/1969 Canada.
0022495 1/1981 European Pat. Off.
0049407 4/1982 European Pat. Off.
0072926 3/1983 European Pat. Off.
0093593 9/1983 European Pat. Off.
150308 7/1970 New Zealand.
1445824 8/1976 United Kingdom.
566842 of 0000 U.S.S.R.

OTHER PUBLICATIONS

Middleton et al, J. Heterocyclic Chem., 17, 1757 (1980).

OPPI Brief, 1980, p. 235.
Nerichte, 71B, 2347–60 (1938).
Haskell et al., J. Med. Chem. (1970) 13(4) 697.

Primary Examiner—Stanley J. Friedman
Attorney, Agent, or Firm—Donald Brown

[57] ABSTRACT

Compounds of formula (I'), and compositions containing them:

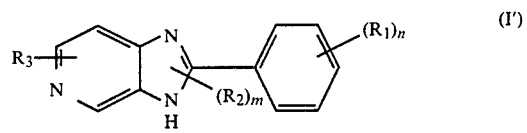

wherein n is 1, 2 or 3, each $R_1$ independently represents a halogen atom; a hydroxy, carboxyl or $C_{1-4}$alkyl group, a $C_{2-4}$alkenyloxy, phenyl or phenyl-$C_{1-4}$alkoxy group which may be optionally substituted by one or more halogen atoms; an amino, mono- or dialkyl-amino, morpholino or piperazino group; a group of formula —S(O)$_x$R$_a$ where x is 0, 1 or 2 and R$_a$ is a $C_{1-4}$alkyl group; or a $C_{1-4}$alkoxy group which may be optionally substituted by one or more radicals selected from hydroxy, $C_{1-4}$alkoxy, amino, mono- or di-$C_{1-4}$alkylamino, (phenyl-$C_{1-4}$alkyl)amino, N,N-$C_{1-4}$alkyl(phenyl-$C_{1-4}$alkyl)amino and N,N-($C_{1-4}$alkoxyphenyl-$C_{1-4}$alkyl)$C_{1-4}$ alkyl-amino; n is 1, 2 or 3; m is 0 or 1; $R_2$ represents a $C_{1-4}$alkyl group in the 1- or 3-position of the imidazo ring; $R_3$ represents a hydrogen or halogen (fluorine, chlorine, bromine or iodine) atom, or a hydroxy, amino or $C_{1-4}$alkyl or alkoxy group; and physiologically acceptable acid addition salts thereof and N-oxides of such compounds and salts. Formula (I') includes the alternative tautomeric form. The compounds and compositions are useful for treatment of the human or animal body by therapy, particularly for use in the treatment or prophylaxis of heart failure and myocardial insufficiency.

2 Claims, No Drawings

BICYCLE COMPOUNDS, PROCESSES FOR THEIR PREPARATION AND PHARMACEUTICAL FORMULATIONS CONTAINING COMPOUNDS

This application is a continuation of application Ser. No 522,995, filed Aug. 15, 1983 which is a division of Ser. No. 440,258 filed Nov. 9, 1982, both now abandoned.

The present invention relates to novel imidazo[4,5-c]pyridine derivatives having positive inotropic activity.

Cardiac glycosides such as digoxin and sympathomimetics have been widely used for many years for the treatment of heart failure. It is, however, well known that these compounds suffer from a number of disadvantages which limit their use in practice as described, for example, by Opie L. H., Drugs and the Heart V and VII, Lancet 1980, i, 912 and 1011; Editorial, Treatments for heart failure: Stimulation or unloading, Lancet 1979, ii, 777; and Braunwald E, Pharmacological treatment of cardiovascular disorders in Harrison's Principles of Internal Medicine, p 1064, ed. Isselbacher et al McGraw-Hill, New York. Another compound which has more recently been proposed for use in the treatment of congestive heart failure is amrinone. Furthermore, U.K. Patent Specification No. 1,445,824 describes certain imidazo[4,5-b]pyridine derivatives which are said in the specification to have positive inotropic activity. Of these compounds, 2-[(2-methoxy-4-methylsulphinyl)phenyl]-1H-imidazo[4,5-b]pyridine, specifically described in the specification, and otherwise known as AR-L 115 BS or Vardax, has been the subject of reports in the literature.

We have now discovered that imidazo[4,5-c]pyridine derivatives of formula (I) below possess advantageous inotropic properties which render the compounds useful for the treatment of heart failure while avoiding or obviating problems associated with the use of previously proposed inotropic agents.

The present invention thus provides compounds of the general formula (I):

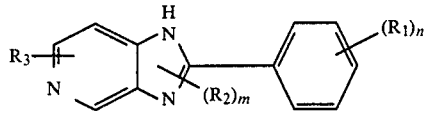
(I)

wherein n is 1, 2 or 3, each $R_1$ independently represents a halogen atom; a hydroxy, carboxyl or $C_{1-4}$alkyl group; a $C_{2-4}$alkenyloxy, phenyl or phenyl-$C_{1-4}$alkoxy group which may be optionally substituted by one or more halogen atoms; an amino, mono- or di-$C_{1-4}$alkyl-amino, morpholino or piperazino group; a group of formula $-S(O)_xR_a$ wherein x is 0, 1 or 2 and $R_a$ is a $C_{1-4}$alkyl group; or a $C_{1-4}$alkoxy group which may be optionally substituted by one or more radicals selected from hydroxy, $C_{1-4}$alkoxy, amino, mono or di-$C_{1-4}$alkylamino, (phenyl-$C_{1-4}$alkyl)amino, N,N-$C_{1-4}$alkyl(phenyl-$C_{1-4}$alkyl)amino and N,N-($C_{1-4}$alkoxyphenyl-$C_{1-4}$alkyl)$C_{1-4}$alkylamino; m is 0 or 1; $R_2$ represents a $C_{1-4}$alkyl group in the 1- or 3-position of the imidazo ring; $R_3$ represents a hydrogen or halogen (fluorine, chlorine, bromine or iodine) atom, or a hydroxy, amino or $C_{1-4}$alkyl or alkoxy group; providing that when n is 1, m is 0 and $R_3$ represents a hydrogen atom, $R_1$ does not represent a 4-methoxy, 4-dimethylamino, 2- or 4-amino, 2-hydroxy or 3 or 4-chloro group.

It will be appreciated that formula (I) may be depicted in the alternative tautomeric form:

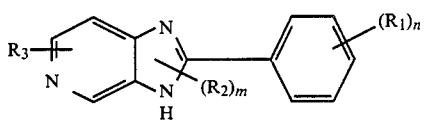

(wherein $R_1$ $R_2$, $R_3$, n and m are as defined above). Thus, references herein to formula (I) should be taken to include, where appropriate, references to the above-mentioned alternative tautomeric form.

Those compounds of formula (I) wherein $R_1$ is a 4-methoxy or 4-dimethylamino group, n is 1, m is 0 and $R_3$ is hydrogen are disclosed in USSR Patent Specification No. 566842. Compounds of formula (I) wherein $R_1$ represents a 3- or 4-chlorine atom or a 2-hydroxy or 4-amino group, n is 1, m is 0 and $R_3$ is hydrogen are described by R. W. Middleton and D. G. Wibberly, J. Heterocyclic Chem. 17, 1957 (1980). A compound of formula (I) wherein $R_1$ is a 2-amino group, n is 1, m is 0 and $R_3$ is hydrogen are disclosed by Maskell et al in J. Med. Chem., 1970, 13(4), 697. These references do not, however, disclose or suggest the use of the compounds for the therapeutic treatment of the human or animal body.

The present invention also includes the acid addition salts of the compounds of formula (I). These salts may be formed by protonation of one or more of the basic nitrogen atoms in formula (I). It will be appreciated that for therapeutic use a physiologically acceptable acid addition salt will be required, for example, a salt derived from hydrochloric, hydrobromic, phosphoric, malic, maleic, fumaric, citric, sulphuric, lactic or tartaric acid. However, the present invention also includes other acid addition salts which may be used for isolating, purifying or characterising the parent compounds of formula (I). The present invention further includes the N-oxides of the compounds of formula (I) and the acid addition salts of such N-oxides.

In general formula (I), $R_1$ may for example represent a methyl, ethyl, allyloxy, benzyloxy, methylthio, methylsulphinyl, methylsulphonyl, methoxy, ethoxy, or propoxy group. $R_2$ may for example represent a methyl or ethyl group while $R_3$ may for example represent a hydrogen or halogen (e.g. chlorine) atom or a methyl, ethyl, methoxy or ethoxy group. In the definitions of $R_1$ and $R_3$, the references to halogen atoms include fluorine, chlorine, bromine, and iodine atoms.

In general, preferred compounds of formula (I) having particularly advantageous inotropic activity include those wherein $R_3$ represents a hydrogen atom, m is 0 and/or those wherein n is 1, 2 or 3.

Preferred $R_1$ groups in formula (I) include halogen atoms (especially chlorine), $C_{2-4}$alkenyloxy groups, especially allyloxy, $C_{1-4}$alkoxy groups, especially methoxy and ethoxy, methoxy being particularly preferred, and groups of formula $-S(O)_xR_a$ (wherein x is 0, 1 or 2, preferably 1, and $R_a$ represents a methyl or ethyl group), especially methylsulphinyl.

Particularly preferred classes of compounds of formula (I) include those wherein m is 0, $R_3$ preferably represents a hydrogen atom and:

(a) in the case where n is 1, the group $R_1$ represents a $C_{1-4}$alkoxy group in the 2- or 4-position or a group of formula $-S(O)_xR_a$ in the 2-position.

(b) in the case where n is 2:
  (i) both $R_1$ groups represent $C_{1-4}$alkoxy groups in the 2,4-, 2,5- or 3,4-positions;
  (ii) one $R_1$ group represents a $C_{1-4}$alkoxy group in the 2-position and the other represents a halogen atom or a group of formula $-S(O)_xR_a$ in the 4-position; or
  (iii) one $R_1$ groups represents a $C_{2-4}$alkenyloxy group in the 2-position and the other represents a $C_{1-4}$alkoxy or $-S(O)_xR_a$ group in the 4-position.

(c) in the case where n is 3, the $R_1$ groups all represent $C_{1-4}$alkoxy groups in the 2,3,4- or 2,4,5- positions.

The compounds according to the invention are useful as cardiotonic agents since they have been found in both in vitro and in vivo experiments to produce a positive inotropic effect at low concentrations, as demonstrated in the tests described hereinafter. Experiments in vivo have also indicated that these effects are long-lasting, and accompanied by a vasodilatory effect. The latter may be of additional benefit in the treatment of heart failure to counteract the marked vasoconstriction which is frequently associated with this condition.

From in vitro and in vivo experiments it is evident that the positive inotropic stimulation caused by these compounds is independent of the myocardial β-adrenoceptors whereas, it has been suggested that at least part of the positive inotropic stimulation caused by the above-mentioned compound Vardax is attributable to stimulation of myocardial β-adrenoceptors (Brutsaert et al, 1982 J. Cardiovasc. Pharmacol. 4, 333–43; Pouleur et al, 1982 J. Cardiovasc. Pharmacol. 4, 409–18).

A further advantage of the compounds according to the invention is that they do not demonstrate any significant myocardial phosphodiesterase inhibitory activity. This contrasts with reports for Vardax which find this compound to be an effective inhibitor of myocardial phosphodiesterase (Diederan and Wiesenberger, 1981, Drug Res. 31(1), 177–82). Phosphodiesterase enzymes are widely distributed throughout the tissues of the body and the administration of an inhibitor, which is inherently non-specific, may result in phosphodiesterase inhibition at sites other than the myocardium, which may be undesirable from the clinical point of view.

The stimulation of myocardial β-adrenoceptors results in an increase in the level of intracellular cAMP, as does the inhibition of myocardial phosphodiesterase. The resultant positive inotropic effects of these interventions are directly linked to the increased levels of cAMP and thus an inotropic stimulation based on either mechanism may be criticised for the same reasons. Both mechanisms are likely to promote myocardial ischaemia through increasing myocardial oxygen demand by their positive chronotropic effects, and in addition evoke arrythmias. In experimental studies it has been found that 2-(2-methoxy-4-methylsulphinylphenyl)-1H-imidazo[4,5-c]pyridine does not exacerbate myocardial injury following selective ligation of the coronary artery in vivo. Furthermore, the last-mentioned compound does not increase ventricular vulnerability to arrythmias in the ischaemic heart.

The compounds according to the invention also possess an inhibitory effect on blood platelet aggregation which could facilitate the treatment of heart failure by providing some protection against the effects of platelet interaction in the myocardium, particularly after infarctions.

A particularly preferred compound by virtue of its advantageous pharmacological properties is 2-(2-methoxy-4-methylsulphinylphenyl)-1H-imidazo[4,5-c]pyridine and its N-oxides and physiologically acceptable acid addition salts.

Other examples of compounds of formula (I) and their acid addition salts include the following bases and their N-oxides and acid addition salts:
2-(2,4-dimethoxyphenyl)-1H-imidazo[4,5-c]pyridine
2-(4-methoxyphenyl)-1H-imidazo[4,5-c]pyridine
2-(3,4,5-trimethoxyphenyl)-1H-imidazo[4,5-c]pyridine
2-(2,3,4-trimethoxyphenyl)-1H-imidazo[4,5-c]pyridine
2-(2-methoxyphenyl)-1H-imidazo[4,5-c]pyridine
2-(3,4-dimethoxyphenyl)-1H-imidazo[4,5-c]pyridine
2-(3,4-diethoxyphenyl)-1H-imidazo[4,5-c]pyridine
2-(2-methoxy-4-chlorophenyl)-1H-imidazo[4,5-c]pyridine
2-(2,5-dimethoxyphenyl)-1H-imidazo[4,5-c]pyridine
2-(2-methylthiophenyl)-1H-imidazo[4,5-c]pyridine
2-(2-methoxy-4-methylsulphonylphenyl)-1H-imidazo[4,5-c]pyridine
2-(2-propyloxy-4-methoxyphenyl)-1H-imidazo[4,5-c]pyridine
2-(2-methoxy-4-methylsulphinylphenyl)-1H-imidazo[4,5-c]pyridine
3-methyl-2-(2,4-dimethoxyphenyl)-1H-imidazo[4,5-c]pyridine
1-methyl-2-(2,4-dimethoxyphenyl)-1H-imidazo[4,5-c]pyridine
2-(2,4,5-trimethoxyphenyl)-1H-imidazo[4,5-c]pyridine
2-(3-methylthio-4-methoxy)-1H-imidazo[4,5-c]pyridine The present invention also provides compounds of formula

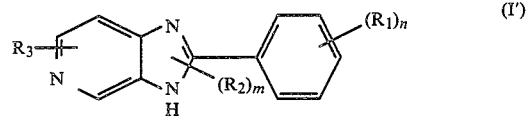

(wherein n is 1, 2 or 3, each $R_1$ independently represents a halogen atom; a hydroxy, carboxyl or $C_{1-4}$alkyl group, a $C_{2-4}$alkenyloxy, phenyl or phenyl-$C_{1-4}$alkoxy group which may be optionally substituted by one or more halogen atoms; an amino, mono- or dialkyl-amino, morpholino or piperazino group; a group of formula $-S(O)_xR_a$ where x is 0, 1 or 2 and $R_a$ is a $C_{1-4}$alkyl group; or a $C_{1-4}$alkoxy group which may be optionally substituted by one or more radicals selected from hydroxy, $C_{1-4}$alkoxy, amino, mono- or di-$C_{1-4}$alkylamino, (phenyl-$C_{1-4}$alkyl)amino, N,N-$C_{1-4}$alkyl(phenyl-$C_{1-4}$alkyl)amino and N,N-($C_{1-4}$alkoxyphenyl-$C_{1-4}$alkyl)$C_{1-4}$alkylamino; n is 1, 2 or 3; m is 0 or 1; $R_2$ represents a $C_{1-4}$alkyl group in the 1- or 3-position of the imidazo ring; $R_3$ represents a hydrogen or halogen (fluorine, chlorine, bromine or iodine) atom, or a hydroxy, amino or $C_{1-4}$alkyl or alkoxy group; and physiologically acceptable acid addition salts thereof and N-oxides of such compounds and salts, for use in a method of treatment of the human or animal body by therapy, particularly for use in the treatment or prophylaxis of heart failure and myocardial insufficiency.

It will be appreciated that formula (I') may be written in a similar alternative tautomeric form to formula (I), as indicated above, and references herein to formula (I')

should also be taken to include, where appropriate, the alternative tautomeric form.

The compounds of formula (I') and their salts and N-oxides may be administered by the oral, rectal or parenteral route. In general, these compounds may be administered at a dosage in the range of 1 to 1200 mg per day although the precise dosage will naturally depend on a number of clinical factors, for example, the type (i.e. human or animal), age and weight of the subject, the condition under treatment and its severity, and the particular compound employed. For administration of the compounds by the oral route, a dosage regime of 100 to 400 mg, e.g. about 200 mg per day may be used, while for administration by the parenteral route, especially intravenously, a dosage regime of 20 to 300 mg, advantageously 35 to 70 mg, e.g. about 50 mg per day is generally preferred. The compounds may be administered intravenously by infusion, if desired, in which case, a dosage rate of, for example, 1–4 mg/min may be employed.

The compounds of formula (I') and their physiologically acceptable acid addition salts and N-oxides of such compounds and salts are preferably administered in the form of pharmaceutical formulations.

The present invention thus further provides pharmaceutically acceptable formulations comprising at least one compound of formula (I') (as defined above) or a physiologically acceptable acid addition salt or an N-oxide of the said compound or salt, in association with at least one pharmaceutical carrier or excipient. The pharmaceutical formulations may be adapted for oral, parenteral (particularly intravenous) or rectal administration. The formulations may conveniently be presented in unit dosage form and may be prepared by any of the methods well known in the art of pharmacy. Such methods include the step of bringing into association the active ingredient with the carrier which may comprise one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for rectal administration may be presented as a suppository with the usual carriers such as cocoa butter.

Formulations suitable for parenteral administration include aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powder, granules and tablets of the kind previously described.

Preferred unit dosage formulations are those containing a daily dose or unit daily sub-dose, as hereinabove recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The compounds of formula (I) and their acid addition salts and N-oxides may be prepared by any convenient process, e.g. using procedures described in the above-mentioned references.

Thus, for example, according to a further feature of the present invention, we provide a process for the preparation of compounds of formula (I) and their N-oxides and acid addition salts which comprises (a) reacting a compound of formula

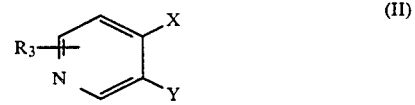

(wherein $R_3$ is as defined above, X and Y which may be the same or different, each represents an amino group, a group of formula $-NHR_2$ (wherein $R_2$ is as defined above) or a displaceable radical, e.g. hydrogen or a halogen atom such as chlorine, providing that X and Y do not both represent displaceable radicals or groups of formula $-NHR_2$) with a compound of formula

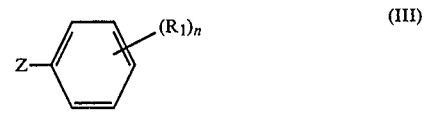

(wherein $R_1$ and n are as defined above and Z represents a group capable of reacting with groups X and Y (sequentially or simultaneously) to form an imidazo ring system with consequential formation of a compound of formula (I) or an acid addition salt thereof; or (b) reacting a compound of formula

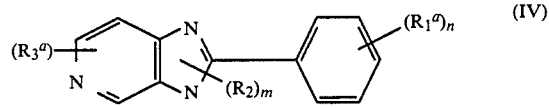

(wherein $R_2$, n and m and are as defined above, each $R_1{}^a$ independently represents a group as defined for $R_1$ above or a precursor group therefor and $R_3{}^a$ represents a group as defined for $R_3$ above or a precursor group therefor, providing at least one of $R_1{}^a$ and $R_3{}^a$ represent such a precursor group) or an acid addition salt thereof with an agent serving to effect conversion of the precursor group(s) for $R_1{}^a$ and/or $R_3{}^a$ into the desired group(s); or (c) radical arylation of a compound of formula

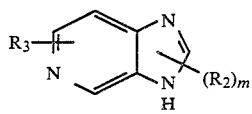
(V)

(wherein $R_2$, $R_3$ and m are as hereinbefore defined) by reaction with a compound of formula

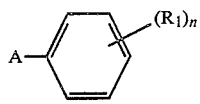
(VI)

(wherein $R_1$ and n are as hereinbefore defined and A represents a displaceable radical, e.g. a diazonium halide, for example the chloride) and where a compound of formula (I) is formed, optionally converting the said compound into an N-oxide or acid addition salt thereof.

The reaction in process (a) may optionally be carried out in a solvent, e.g. an organic solvent for example, ethylene glycol, conveniently at a elevated temperature, e.g. up to the reflux temperature of the reaction mixture.

According to a preferred embodiment of process (a) above according to the invention, a compound of formula (II) (wherein $R_3$ is as hereinbefore defined and either X and Y both represent amino groups or one of X and Y represents an amino group and the other represents a group of formula —$NHR_2$) is reacted with a compound of formula (III) (wherein $R_1$ and n are as hereinbefore defined and Z is a carboxyl, thiocarboxyl or dithiocarboxyl group) or a functional equivalent thereof (e.g. an acid halide, acid anhydride, amide, thioamide, imidate, thioimidate or ester thereof) or an aldehyde or nitrile thereof.

When a compound of formula (III) is employed, wherein Z represents a free carboxylic acid group, the reaction is advantageously effected in the presence of a dehydrating agent such as phosphorus oxychloride. Alternatively, the reaction may be effected in the presence of polyphosphoric acid. When a compound of formula (III) is employed, wherein Z represents an acid halide, the reaction is advantageously effected in the presence of an acid binding agent e.g. a tertiary base such as triethylamine. Where a nitrile of a compound of formula (III) is employed, the reaction is advantageously effected in the presence of an acid, e.g. p-toluenesulphonic acid or polyphosphoric acid.

Alternatively, a compound of formula (III) (wherein Z represents an aldehyde group) may be employed, in which case the reaction may be effected for example, as described by R. Weidenhagen et al, Chem. Ber. 1942, 75, 1936 or in USSR Patent Specification No. 566842. Thus, for example following the procedure described in the last-mentioned Patent Specification, a compound of formula (II) (wherein X and Y both represent amino groups) may be reacted with an aldehyde compound of formula (III) in the presence of sulphur.

In one example of the preferred embodiment above, the compound of formula (II) may be reacted with a thioamide of a compound of formula (III), e.g. a thiomorpholide which is advantageously employed in the form of a quaternised product thereof, e.g. the appropriate S-methyl-thiobenzyl morpholide iodide. Alternatively, the compound of formula (III) may be employed in the form of a morpholide.

A further preferred embodiment of process (a) according to the present invention comprises reacting a compound of formula (II) (wherein $R_3$ is as hereinbefore defined, one of X and Y represents a halogen atom and the other represents an amino group or a group of formula —$NHR_2$ (wherein $R_2$ is as hereinbefore defined)) with a compound of formula (III) (wherein $R_1$ and n are as hereinbefore defined and Z represents an amino-or $NHR_2$-containing group derived from a carboxyl group, e.g. a $H_2NCO$-group.

In process (a), the Z group in the compound of formula (III) may react sequentially with groups X and Y in the compound of formula (II), e.g. with the initial formation of a compound of formula

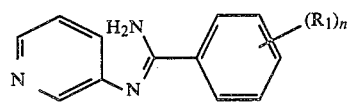
(VII)

(wherein $R_1$ and n are as hereinbefore defined) which may subsequently be cyclised, eg. by treatment with lead tetra-acetate to form a compound of formula (I).

With regard to process (b) above, those compounds of formula (I) wherein $R_3$ represents an amino group may be prepared for example by treatment of a corresponding compound wherein $R_3$ represents chlorine atom with aqueous ammonia while compounds wherein $R_3$ represents hydroxy may be prepared by treatment of a corresponding compound wherein $R_3$ represents an amino group by treatment with nitrous acid. Compounds of formula (I) wherein $R_3$ represents $C_{1-4}$alkoxy group may for example be prepared by alkoxylation of a corresponding compound wherein $R_3$ represents a chlorine atom.

Compounds of formula (I) wherein $R_1$ represents a $C_{1-4}$alkyl-sulphinyl or -sulphonyl group may be prepared for example by oxidation, e.g. using hydrogen peroxide, organic peracids, or bromine or one of its addition compounds, eg. an alkali metal hypobromite, as described in German Offenlegungsschrift DE No. 3044 497 of the corresponding $C_{1-4}$alkylthio compound.

Compounds wherein $R_1$ represents a hydroxy group may be prepared for example by treatment with boron tribromide of the corresponding methoxy compounds.

Compounds wherein $R_1$ represents a methoxy group may be prepared by treatment of a corresponding compound wherein $R_1$ represents a hydroxy group, with a methylating agent, e.g. methyl sulphate.

Compounds wherein $R_1$ represents a $C_{1-4}$alkylthio group may be prepared by diazotisation of a corresponding compound wherein $R_1$ represents an amino group (e.g. by treatment with nitrous acid), followed by reaction of the product with an appropriate $C_{1-4}$alkyl mercaptan.

The radical arylation in process (c) above may be conveniently effected by the general method of M-H Hung and L. M. Stock, J. Org. Chem., 1982, 47, 448-453. When the compound of formula (VI) is employed in the form of diazonium salt, this salt may be prepared in conventional manner e.g. from the corresponding amino compound.

The acid addition salts of the compounds of formula (I) may be prepared in conventional manner, e.g. by treatment of the free base with an appropriate acid. The N-oxides of the compounds of formula (I) may also be prepared in conventional manner e.g. by oxidation of the parent compound with an appropriate oxidising agent, eg. m-chloroperbenzoic acid.

The following examples illustrate the present invention.

EXAMPLE 1

2-(2,4-Dimethoxyphenyl)-1H-imidazo[4,5-c]pyridine

A mixture of 2,4 dimethoxybenzoic acid (2.5 g) and 3,4-diaminopyridine (1.5 g) was ground to a fine powder and added portionwise to phosphorus oxychloride (50 ml) with stirring. The mixture was stirred and heated under reflux for 2.5 hours before excess phosphorus oxychloride was removed in vacuo. The residue was cooled, water (20 ml) added and the pH adjusted to 7 with ammonium hydroxide to yield a pale yellow solid which was collected, washed with water and dried. The solid was recrystallised twice from aqueous ethanol to yield a cream coloured crystalline solid m.p. 195°–198°.

Analysis: Calc. C, 65.88; H, 5.09; N, 16.47. Found: C, 65.70, H, 5.15; N, 16.05.

The structure was confirmed by N.M.R. and M.S. data

EXAMPLE 2

2-(4-Methoxyphenyl)-1H-imidazo[4,5-c]pyridine dihydrochloride

A mixture of 3,4-diaminopyridine (1.5 g) and 4-methoxybenzoic acid (2.1 g) were ground up to a powder and added portionwise to phosphorus oxychloride (50 ml) with stirring.

The mixture was heated under reflux for 2.5 hr before the excess oxychloride was removed in vacuo. The residue was cooled, water (20 ml) added and pH adjusted to 7 with 1N NaOH to yield a pale yellow solid which was collected, washed with water, and dried. Recrystallisation from aqueous ethanol gave a pale yellow crystalline solid 1.06 g.

The solid was taken up in hot acetone (30 ml) and the insoluble material removed by filtration; the filtrate was treated with ethereal HCl to precipitate the dihydrochloride salt which was collected, washed with dry ether and dried m.p. 263°–266°.

EXAMPLES 3–22

In an analogous manner to that described in Example 1, the following compounds were prepared:
(3) 2-(3,4,5-trimethoxyphenyl)-1H-imidazo[4,5-c]pyridine dihydrochloride, m.p. 250°–254° C.
(4) 2-(2-methoxy-4-methylthiophenyl)-1H-imidazo[4,5-c]pyridine dihydrochloride, m.p. 205°–206° C.
(5) 2-(2,3,4-trimethoxyphenyl)-1H-imidazo[4,5-c]pyridine dihydrochloride, m.p. 250°–252° C. (dec)
(6) 2-(2-methylaminophenyl)-1H-imidazo[4,5-c]pyridine hydrochloride, m.p. 218°–221° C.
(7) 2-(2-methoxyphenyl)-1H-imidazo[4,5-c]pyridine hydrochloride, m.p. 190°–194° C.
(8) 2-(3,4-dimethoxyphenyl)-1H-imidazo[4,5-c]pyridine dihydrochloride, m.p. 262° C. (decomp)
(9) 2-(3,4-diethoxyphenyl)-1H-imidazo[4,5-c]pyridine dihydrochloride, m.p. 259°–260° C.
(10) 2-(2-methoxy-4-chlorophenyl)-1H-imidazo[4,5-c]pyridine hydrochloride, m.p. 185°–191° C.
(11) 2-(2-propyloxy-4-methoxyphenyl)-1H-imidazo[4,5-c]pyridine hydrochloride, m.p. 228°–231° C.
(12) 2-(2,4-dimethylphenyl)-1H-imidazo[4,5-c]pyridine, m.p. 108°–12° C. and its hydrochloride, m.p. 288°–292° C.
(13) 2-[2-(2-methoxyethoxy)-4-methoxyphenyl]-1H-imidazo[4,5-c]pyridine, m.p. 130°–132° C. and its hydrochloride, m.p. 211°–214° C.

The following compounds and their salts are also prepared in an analogous manner:
(14) 2-(2-methoxy-5-methylthiophenyl)-1H-imidazo[4,5-c]pyridine
(15) 2-(2-methoxy-5-methylsulphinylphenyl)-1H-imidazo[4,5-c]pyridine
(16) 2-(2-methoxy-4-carboxyphenyl)-1H-imidazo[4,5-c]pyridine
(17) 2-(2-methoxy-4-fluorophenyl)-1H-imidazo[4,5-c]pyridine
(18) 2-(2-methoxy-4-aminophenyl)-1H-imidazo[4,5-c]pyridine
(19) 2-(2,4-dimethoxyphenyl)-4-methyl-1H-imidazo[4,5-c]pyridine
(20) 2-(2,4-dimethoxyphenyl)-7-methyl-1H-imidazo[4,5-c]pyridine

EXAMPLE 21

2-(2-Methoxy-4-methylsulphinylphenyl)-1H-imidazo[4,5-c]pyridine

To a mixture of acetic acid (20 ml), water (6 ml) and hydrogen peroxide (30% solution) (2.5 eq), while stirring at room temperature, was added, in portions, the compound of Example 4 (1.5 g). The reaction mixture was stirred at room temperature for 2 hours and allowed to stand overnight at 4° C. Tlc indicated that the reaction was complete. The resulting mixture was poured into water (25 ml), basified with 0.88 ammonia and extracted with chloroform. The organic extract was dried, decolourised and evaporated in vacuo to a foam which was crystallised from ethyl acetate/acetone to give the title compound, m.p. 202°–204° C.

In an alternative preparation, the title compound was prepared as follows:

To a stirred and cooled suspension of the compound of Example 4 (18 g) and sodium acetate (1 eq) in glacial acetic acid was added bromine (3.2 ml) in glacial acetic acid at such a rate that the temperature was held below about 5° C. The mixture was poured into 100 g crushed ice and the pH adjusted to 9 with 0.88 ammonia. The resulting solution (containing some brown solid) was saturated with sodium chloride and extracted with chloroform (4×300 ml). The combined chloroform extracts were dried, decolourised with animal charcoal and evaporated in vacuo to a froth which on trituration with ether gave the title product.

EXAMPLE 22

2-(2-Methylsulphinyl-4-methoxyphenyl)-1H-imidazo[4,5-c]pyridine hydrochloride

Using the method of Example 21, and starting from 2-(2-methylthio-4-methoxyphenyl)-1H-imidazo[4,5-c]pyridine, the title compound was prepared in analogous manner.

EXAMPLE 23

2-(2-Methoxy-4-methylsulphinylphenyl)-1H-imidazo[4,5-c]pyridine hydrochloride

The compound of Example 21 was suspended in ether and dry hydrogen chloride gas was bubbled through the suspension for about 2 minutes. The insoluble solid was filtered off and dried to give the title compound as a white solid, m.p. 153°–155° C.

EXAMPLE 24

2-(2,5-Dimethoxyphenyl)-1H-imidazo[4,5-c]pyridine dihydrochloride 2,5-Dimethoxybenzaldehyde, morpholine and sulphur were heated for 3 hours at 120° C. The solid mixture melted to give a liquid. The reaction mixture was cooled and dissolved in hot methanol. On cooling the methanol solution, solid (thiomorpholide) resulted which was filtered and dried. The thiomorpholide was refluxed for about 2 hours in acetone with methyl iodide (1.2 equivalents). Acetone was then removed in vacuo to give a brown viscous oil (thiomorpholide methiodide) which was mixed with 3,4-diaminopyridine in ethylene glycol and the mixture heated at 120° C. for 2 hours. The reaction mixture was diluted with water and the solid obtained was filtered off, suspended in water and basified with 0.88 ammonia. The solid was filtered off, dried and converted to the title dihydrochloride salt, m.p. 188°–190° C. (decomp).

EXAMPLE 25

2-(2,4-Dimethoxy-3-methylthiophenyl)-1H-imidazo[4,5-c]pyridine hydrochloride

The title compound was made in an analogous manner to that of Example 24, m.p. 205°–207° C.

EXAMPLE 26

2-(2,4-Dimethoxy-3-methylsulphinylphenyl)-1H-imidazo[4,5-c]pyridine

The title compound is made from the compound of Example 25, by a method analogous to that described in Example 21.

EXAMPLES 27–30

The following compounds, namely:
(27) 2-(4-biphenyl-4-yl)-1H-imidazo[4,5-c]pyridine 1.5 hydrochloride, m.p. 352°–355° C.,
(28) 2-(2,4-dichlorophenyl)-1H-imidazo[4,5-c]pyridine hydrochloride, m.p. 230°–232° C.,
(29) 2-(2-methylthiophenyl)-1H-imidazo[4,5-c]pyridine hydrochloride, m.p. 158°–160° C.
(30) 2-(3-methylthiophenyl)-1H-imidazo[4,5-c]pyridine dihydrochloride, m.p. 123.5°–125° C.
(31) 2-(4-methylthiophenyl)-1H-imidazo[4,5-c]pyridine dihydrochloride, m.p. 301°–303° C.
were prepared according to the following general procedure:

The appropriate diaminopyridine was pulverised with the appropriate substituted benzoic acid and the mixture was added portionwise to polyphosphoric acid. The resulting reaction mixture was heated at 180° for about 3 hours. The cooled reaction mixture was poured onto ice, and the precipitated solid was filtered off, suspended in water and neutralised with 0.88 ammonia. The solid so obtained was filtered, dried and converted to the hydrochloride salt.

EXAMPLE 32

2-(2-Methoxy-4-methylsulphonylphenyl)-1H-imidazo[4,5-c]pyridine and its hydrochloride 2-(2-Methoxy-4-methylthiophenyl)-1H-imidazo[4,5-c]pyridine was added portionwise to a stirred solution of 30% hydrogen peroxide in glacial acetic acid and water. The clear brown solution was stirred at 70° C. for 3 hours. T.l.c. indicated the reaction to be complete. The reaction mixture was evaporated in vacuo to remove solvents and the residue was purified by column chromatography to the title free base, m.p. 225°–227° C. The free base obtained above was suspended in methanol and dry hydrogen chloride gas was bubbled through the solution. The solid was filtered off and dried to yield the title hydrochloride, m.p. 221°–223° C. (decomp).

EXAMPLE 33

2-(2-Hydroxy-4-methylthiophenyl)-1H-imidazo[4,5-c]pyridine dihydrochloride 2-(2-Methoxy-4-methylthiophenyl-1H-imidazo[4,5-c]pyridine was suspended in dry dichloromethane and a solution of boron tribromide (3 eq) in dry dichloromethane was added slowly at room temperature. The mixture was refluxed for 5 hours and was then poured into water and basified with 0.88 ammonia. The resulting solution was extracted with chloroform. T.l.c. indicated the product to be in the aqueous layer which was evaporated down to a low bulk when a brown solid precipitated. The solid was extracted into hot methanol and decolourised and evaporated to give a brown solid which was converted to the title dihydrochloride, m.p. 297°–300° C.

EXAMPLE 34

2-(3-Methylthio-4-methoxyphenyl)-1H-imidazo-[4,5-c]pyridine dihydrochloride

3-Methylthio-4-methoxybenzoic acid (obtained by diazotization of 3-amino-4-methoxybenzoic acid, followed by treatment with methylmercaptan) was suspended in dry toluene and thionyl chloride (1.1 eq) was added slowly to it. The mixture was refluxed for 3.5 hours. T.l.c. indicated reaction to be complete. The solvent was removed in vacuo to leave a dark brown residue.

The acid chloride obtained above was suspended in the minimum quantity of dry ether and added portionwise to a suspension of 3,4-diaminopyridine (1 eq) in dry pyridine and triethylamine. The resulting mixture was refluxed for 5 hours. T.l.c. indicated the reaction to be complete.

The cooled reaction mixture was filtered through hyflo and the filtrate evaporated in vacuo. The residue was triturated with ether and then dissolved in methanol.

The solid that separated was filtered off and the methanol filtrate was evaporated under reduced pressure to give a viscous oil. NMR indicated this to consist mainly of the intermediate amide. This oil was dissolved in ethylene glycol and the solution obtained heated at 200° for 4 hours. T.l.c. indicated reaction to be complete.

The cooled reaction mixture was poured into water. A white solid precipitated and was filtered and dried. The solid was triturated into ethyl acetate/ether to give

EXAMPLE 35

2-(3-Methylsulphinyl-4-methoxyphenyl)-1H-imidazo[4,5-c]pyridine

The compound obtained in Example 34, was oxidised using hydrogen peroxide (2 eq) in a manner analogous to that described in Example 21. The title compound was obtained as a white solid, m.p. 227°–229° C.

EXAMPLE 36

2-(3-Methylsulphinylphenyl)-1H-imidazo[4,5-c]pyridine hydrochloride

The compound prepared in Example 30, was oxidised by the method described in Example 23 above, to obtain the title compound as a white solid, m.p. 250°–252° C.

EXAMPLE 37

2-(2-Allyloxy-4-methoxyphenyl)-1H-imidazo[4,5-c]pyridine hydrochloride (a) 2-Allyloxy-4-methoxybenzoyl morpholide To a stirred solution of 2-allyloxy-4-methoxy benzoyl chloride (14 g) in dry toluene was added morpholine (12 ml) and stirring continued for 1 hour.

Toluene was removed under reduced pressure, 2N hydrochloric acid (20 ml) was added to the residue and the mixture was extracted with ethyl acetate. The combined extracts were washed successively with sodium bicarbonate solution and water and dried over magnesium sulphate before filtering and evaporating to yield a yellow oil.

(Purity was certified by thin layer chromatography and the structure confirmed by N.M.R.)

(b) 2-(2-Allyloxy-4-methoxyphenyl)-1H-imidazo[4,5-c]pyridine hydrochloride

To a mixture of 2-allyloxy-4-methoxybenzoyl morpholide (9 g) and 3,4-diaminopyridine (3.9 g) was added dropwise, with stirring, phosphorus oxychloride (16.5 ml).

The mixture was heated under reflux for 3 hours before excess phosphorus oxychloride was removed under reduced pressure. Water (50 ml) was added to the residue and the solution made alkaline with ammonia before extraction with chloroform. The combined extracts were dried over magnesium sulphate before filtering and evaporating to yield a beige coloured solid which was purified by column chromatography (silica gel; chloroform/methanol, 19:1) to give the free base (m.p. 123°–125° C.) of the title compound. The free base was taken up in acetone and treated with ethereal hydrochloric acid to precipitate the hydrochloride salt, m.p. 175°–180° C. (decomp).

EXAMPLE 38

2-(2,4-Dimethoxyphenyl)-1H-imidazo[4,5-c]pyridineN$^5$-oxide hydrate

To a solution of 2 equivalents of m-chloroperbenzoic acid in methylene chloride at room temperature was added 2-(2,4-dimethoxy-phenyl)-1H-imidazo[4,5-c]pyridine. After stirring for 1 hour the yellow solution was refluxed for a further 3 hours. It was then concentrated and chromatographed directly on silica gel, eluting with chloroform-methanol mixtures. Recrystallisation from ethanol-petrol gave the title compound, m.p. 224°–225° C. (dec).

EXAMPLE 39

2-(2,4-Dimethoxyphenyl)-4-chloro-1H-imidazo[4,5-c]pyridine

A suspension in phosphorus oxychloride of the N-oxide obtained in the preceding Example was stirred at 80° C. for 3 hours. Excess phosphorus oxychloride was then removed in vacuo and the residue partitioned between chloroform and dilute ammonium hydroxide. After drying the organic phase over magnesium sulphate, the solvent was evaporated and the residue recrystallised from aqueous ethanol, m.p. 203°–204° C.

EXAMPLE 40

3-Methyl-2-(2,4-dimethoxyphenyl)-1H-imidazo[4,5-c]pyridine and its hydrochloride A mixture of 2,4-dimethoxybenzoic acid and 3-methylamino-4-amino-pyridine (prepared from 3-bromo-4-nitropyridine-N-oxide and methylamine followed by reduction) in phosphorus oxychloride was refluxed for 4 hours. After cooling the solid was triturated with ether and then partitioned between chloroform and saturated sodium bicarbonate. After drying over magnesium sulphate the solvent was evaporated and the residue chromatographed on silica gel. Recrystallisation from benzene-petrol gave the title base, m.p. 162°–163° C. An acetone solution of the base was treated with ethereal HCl to give the title hydrochloride, m.p. 235°–237° C.

EXAMPLE 41

1-Methyl-2-(2,4-dimethoxyphenyl)-1H-imidazo[4,5-c]pyridine and its dihydrochloride The title base was prepared from 4-methylamino-3-amino-pyridine (prepared from 4-chloro-3-nitropyridine and methylamine followed by reduction) and 2,4-dimethoxybenzoic acid in phosphorus oxychloride as described in Example 40, m.p. 180°–181° C. An acetone solution of the base was treated with ethereal HCl to give the title hydrochloride m.p. 225°–227° C.

EXAMPLE 42

2-(3,4-Dihydroxyphenyl)-1H-imidazo[4,5-c]pyridine hydrochloride 2-(3,4-Dimethoxyphenyl)-1H-imidazo[4,5-c]pyridine was stirred at reflux in glacial acetic acid and 48% HBr for 8 hours. After cooling, the precipitate was filtered and recrystallised from 2N HCl to give the title compound m.p. 320°–323° C. (dec).

EXAMPLE 43

2-[4-Methoxy-2-(3-dimethylaminopropoxy)phenyl]-pyridine hydrochloride (a) 2-[4-Methoxy-2-(3-chloropropoxy)phenyl]-1H-imidazo[4,5-c]pyridine A mixture of 3,4-diaminopyridine and 2-(3-chloropropoxy)-4-methoxybenzoic acid in phosphorus oxychloride was stirred at reflux for 4 hours. The excess phosphorus oxychloride was then removed in vacuo and the residue carefully treated with water before basifying with dilute ammonia hydroxide and extracting with chloroform. The crude product was then dissolved in ethyl acetate, decolourised with charcoal and triturated with ethereal HCl to give the title compound m.p. 174°–176° C.

(b)

2-[4-Methoxy-2-(3-dimethylaminopropoxy)phenyl]-1H-imidazo-[4,5-c]-pyridine hydrochloride A solution of the compound obtained in stage (a) in 33% dimethylamine/ethanol was stirred at 100° C. for 8 hours. The volatiles were then removed in vacuo and the residue partitioned between chloroform and saturated sodium bicarbonate. After drying over magnesium sulphate, the solvent was evaporated and the residue recrystallised from benzene/petrol to give the title base. The ethanol solution of the base was treated with ethereal HCl to give the title hydrochloride as a hydrate, m.p. 206°–208° C.

EXAMPLE 44

2-[4-Methoxy-2-(3-iso-propylamino-propoxy)phenyl]-1H-imidazo-[4,5-c]pyridine hydrochloride The above compound was prepared by reacting the product of stage (a) of Example 42 and isopropylamine in ethanol at 100° C. for 8 hours as described in stage (b) of Example 43, m.p. 217°–219° C. (hydrate).

EXAMPLE 45

2-[4-Methoxy-2-(3-tert-butylaminopropoxy)phenyl]1H-imidazo-[4,5-c]pyridine hydrochloride The above compound was prepared by reacting the product of stage (a) of Example 43 and tert-butylamine in ethanol at 100° C. for 8 hours as described in stage (b) in Example 43, m.p. 252°–253° C. (hydrate).

EXAMPLE 46

2-(2,4-Dimethoxyphenyl)-4-amino-1H-imidazo[4,5-c]pyridine

The compound is prepared by treatment of the corresponding 4-chloro compound with ammonium hydroxide.

EXAMPLE 47

2-(2,4-Dimethoxyphenyl)-4-hydroxy-1H-imidazo[4,5-c]pyridine

This compound is prepared by treatment of the corresponding 4-amino compound with nitrous acid.

EXAMPLE 48

2-(2,4-Dimethoxyphenyl)-4-methoxy-1H-imidazo[4,5-c]pyridine

This compound is prepared by 4-methoxylation of the corresponding 4-chloro compound.

EXAMPLE 49

2-(2,4,5-trimethoxyphenyl)-1H-imidazo[4,5-c]pyridine dihydrochloride

This compound was prepared in an analogous manner to that described in Example 1, m.p. 258°–260° C.

EXAMPLE 50

2-(2-methylsulphinyl)-1H-imidazo[4,5-c]pyridine hydrochloride

This compound was prepared from the compound of Example 29, in an analogous manner to that described in Example 21, m.p. 243°–245° C.

The following examples illustrate pharmaceutical formulations according to the present invention wherein the active compound may be any compound of formula (I') defined above, for example, 2-(2-methoxy-4-methylsulphinylphenyl)-1H-imidazo[4,5-c]pyridine.

EXAMPLE A

Tablet Formulation

| | |
|---|---|
| Active compound (as base) | 100 mg |
| Lactose | 100 mg |
| Sodium starch glycollate | 20 mg |
| Polyvinylpyrrolidone | 4 mg |
| Magnesium stearate | 2 mg |
| | 226 mg |

Mix the active compound with the lactose and the sodium starch glycollate. Granulate the mixture with a solution of polyvinylpyrrolidone in 50% aqueous alcohol. Dry the granulate and mix in the magnesium stearate. Compress to tablets of average weight 226 mg.

EXAMPLE B

Capsule Formulation

| | |
|---|---|
| Active compound (as base) | 100 mg |
| Lactose | 100 mg |
| Starch | 30 mg |
| Methylcellulose | 4 mg |
| Stearic Acid | 4 mg |
| | 238 mg |

Mix the active compound with the lactose and the starch. Granulate with a solution of the methylcellulose in water. Dry and mix in the stearic acid.

Fill 238 mg into a hard gelatin capsule.

EXAMPLE C

IV Injection (Freeze Dried)

| | |
|---|---|
| Active compound (as hydrochloride) | 50 mg |
| Mannitol | 50 mg |
| Water for Injection to | 2 ml |

Dissolve the active compound in the Water for Injections. Sterilise the solution by passage through a membrane filter, 0.2μ pore size, collecting the filtrate in a sterile glass receiver. Fill into sterile glass 2 ml vials under aseptic conditions and secure with aluminium seals.

The injection is reconstituted before administration by the addition of a convenient volume of Water for Injection or sterile saline solution when a large volume infusion is required.

EXAMPLE D

IV Injection (Multidose vial)

| | |
|---|---|
| Active compound (as hydrochloride) | 250 mg |
| Benzyl Alcohol | 0.075 ml |
| Water for Injection | 5 ml |

Dissolve the benzyl alcohol in Water for Injection. Add and dissolve the active compound. Make up to volume with Water for Injection. Pass through a membrane filter, 0.2μ pore size, collecting the filtrate in a sterile glass receiver. Fill into sterile glass vials. Close the vials with sterile rubber closures and secure with aluminium seals.

EXAMPLE E

Suppository

| Compound (as base) | 100 mg |
| --- | --- |
| Suppository Base (Massa Esterinum C) to | 2 g |

Melt the suppository base at 40° C. Incorporate the active compound in fine powder form in the molten base and mix until homogeneous. Pour the mixture into suitable moulds, 2 g per mould and allow to set.

BIOLOGICAL ACTIVITY

Determination of in vitro Inotropic Activity

Male guinea-pigs (Halls 275–350 g) having been allowed free access to food and water were killed by a blow to the head. The heart was rapidly excised and washed with Krebs-Henesleit solution containing the β-adrenoceptor antagonist carazolol ($5 \times 10^{-8}$M) and gassed with 95% $O_2$: 5% $CO_2$ at 34° C. The heat was transferred to a petri dish containing the same buffer kept at a constant temperature (34° C.) throughout the dissection. Fresh buffer was used for each dissection and washings were discarded after use. A single right ventricular papillary muscle was employed from each heart; the tendinous end ligated to a stainless steel hook and the lower end ligated and cut away from the ventricle wall and attached to a perspex clamp such that the tissue was in contact with a platinum punctate electrode. The stainless steel hook was suspended from a Grass FT.03 transducer which recorded isometric tension. The preparation was placed in a 20 ml pyrex organ bath containing buffer gassed with 95% $O_2$: 5% $CO_2$ and maintained at 34° C. 500 mg loading tension was applied to the preparation. Stimulation was effected by rectangular pulses of 1msec duration at 1.5 Hz at 30% above the threshold voltage (1–5 volts) by a SRI stimulator. The transducer inputs were coupled to a potentiometric recording device by a 6-channel Grass transducer coupler. After 90 minutes, preparations unable to sustain uniform contractions beyond this period were rejected. After observing both a stable baseline and contractile force (usually 15 minutes) additions of test compounds were made in a cumulative fashion in 0.5 $log_{10}$ unit intervals over the range of $10^{-9}$M to $>10^{-3}$M (final bath concentration) or the limit of solubility which ever is the greater.

The following compounds were tested and found, in the concentration range specified above, to have positive inotropic activity and to be capable of eliciting at least 75% increase in the basal contractile force ($F_c$). The compounds may be ranked as follows:

| Potency for 75% increase $F_c$ lying within the range: | Compounds of Example Nos: |
| --- | --- |
| (1) $>10^{-3}$ M | 3,22,35,38,40,41,50 |
| (2) $10^{-4}$–$10^{-3}$ M | 1,7,21,23,29,32,34 |
| (3) $10^{-5}$–$10^{-4}$ | 8,10 |

Determination of in vivo Inotropic and Vasodilatory Activity

The compounds of Examples 1,2 and 21 were tested in comparison with amrinone and Vardax. In anaesthetised, open-chest beagles, bolus intravenous injections of the test compound (see Table below) produce a dose-related positive inotropic stimulation (as measured by the increase in the rate of change of the left ventricular pressure—dp/dt) over the dose range of 0.003–3.0 mg/kg. This is accompanied by a dose-related increase in aortic blood flow, and a fall in systemic blood pressure (see Table below).

| Compound | $ED_{50}$INO | $ED_{30}$VASO |
| --- | --- | --- |
| Example 2 | 2.0 mg/kg | 5.1 mg/kg |
| Example 1 | 0.13 mg/kg | 0.24 mg/kg |
| Example 21 | 0.063 mg/kg | 0.19 mg/kg |
| Vardax | 1.0 mg/kg | 2.11 mg/kg |
| Amrinone | 1.0 mg/kg | 2.0 mg/kg |

Determination of Phosphodiesterase Inhibitory Activity

The determination of phosphodiesterase inhibitory activity was effected by a procedure based on that of Thompson and Appleman (Biochme., 10, 311 (1971)). $^3$H-cAMP (5 uM) is incubated at 37° C. for 30 minutes with the 1000Xg supernatent of a 10% (w/v) homogenate of guinea pig heart in 50 mM-Tris/HCL pH7+5 mM—mgCl$_2$ in either the presence or the absence of the compound of Example 21 which, in the former case, is dissolved in Tris buffer to give final concentrations of 100 uM, 1 mM and 10 mM. Phosphodiesterase enzyme in the homogenate hydrolyses $^3$H-cAMP to $^3$H-5'-AMP which is further converted to $^3$H-adenosine by a 5'-nucleotidase added to the incubation mixture. After a period of incubation unchanged $^3$H-cAMP is removed by adding ion exchange resin to the mixture and centrifuging. The $^3$H in the supernatent is assayed by liquid scintillation counting and gives a quantitative measure of adenosine formation (i.e. cAMP hydrolysis). Comparison of the $^3$H-adenosine formed in the presence and absence of test compound gives a measure of the PDE-inhibitory activity of the compound. At 100 μM, 1 mM and 10 mM, the compound of Example 21 exhibited no PDE inhibitory activity.

Cardiovascular and anti-aggregating actions of the compound of Example 21 (Compound A) in the anaesthetised rhesus monkey Rhesus monkeys of both sexes (7.3–9 kg, body weight) were sedated with phencyclidine, subsequently anaesthetised with thiopentone and maintained with sodium pentobarbitone. Catheters were placed in the left femoral artery to record blood pressure and in the left femoral vein for administration of drugs. A further catheter was placed in the contralateral femoral artery for the removal of blood samples. Heart rate was recorded from ECG (standard lead II). A left ventricular catheter was introduced via the left carotid artery to measure left ventricular pressure. All cardiovascular parameters were displayed on a polygraph (Grass, model 7D). Rectal temperature of the anaesthetised monkey was maintained at 37°–38° C. via a heated table-pad.

(i) Ex vivo inhibition of platelet aggregation

Blood samples (3 ml) were withdrawn into syringes containing trisodium citrate (0.315% w/v final concentration), and spun for 2 seconds. The platelet rich-plasma was transferred to a Born-type aggregometer and incubated for 1 min (at 37° C.) prior to the addition of sufficient ADP to induce sub-maximal (1.5–3 μM) or near maximal (8–12 μM) aggregation. Inhibition of aggregation was calculated with reference to at least 2 control samples prior to intravenous infusion of compound A. The sequence of administration of compound A was randomized between experiments. The effective dose of compound A which caused 50% inhibition of aggregation is 1.0 mg/kg i.v. (approximately).

(ii) In vitro inhibition of platelet aggregation

Blood was freshly collected into siliconized (Siloclad; Clay Adams) plastic (Sterlin Ltd.) tubes containing trisodium citrate (3.15%; 0.1 volume with 0.9 volume blood) and centrifuged (200 g for 15 min) at room temperature. The platelet-rich plasma (PRP) was withdrawn into plastic containers and kept at room temperature. Inhibition of platelet aggregation was determined in a Born-type aggregometer by incubating aliquots (0.5 ml) of the PRP for 1 min at 37° C. with or without compound A prior to addition of sufficient adenosine diphosphate (ADP). Dose-inhibition curves were constructed for each compound and the $ID_{50}$ (dose causing 50% inhibition) was calculated as the dose required to reduce the aggregation to 50% of its control amplitude. The $ID_{50}$ for compound A is 1 mg/ml (approximately).

Toxicity Studies

In preliminary toxicity studies, the effects of intravenous administration of compound A (see above) to female Wistar rats has been determined.

Animals were randomly distributed into groups of five, each group receiving a single administration of drug. One group served as a control and received the vehicle only. Observations on behaviour were made at 5 minutes and 20 minutes, at 1, 3, 4½ hours and at 2, 4 and 6 days following drug administration.

The findings of these studies are tabulated below.

| DOSE | OBSERVATION | MORTALITY |
|---|---|---|
| 35 mg/kg | Flushing, Slight hypothermia (<1° C.) | — |
| 70 mg/kg | Hypoactivity, ataxia, slow respiration | — |
| 100 mg/kg | Hypothermia (<2° C.) deep slow respiration, ataxia, flushing, hypoactivity | — |
| 140 mg/kg | Hypoactivity, hypothermia, (2–3° C.) ataxia | 2/5 within 3h  4/5 within 2 days |
| 200 mg/kg | Hypoactivity, ataxia, convulsions | 5/5 within 5–30 minutes |

I claim:

1. A method of inhibiting blood platelet aggregation in a human in need thereof, which comprises administering to said human an effective blood platelet aggregation inhibition amount of a compound 2-(2-methoxy-4-methylsulphinylphenyl)-1H-imidazo[4,5-c]pyridine, or a pharmacologically acceptable acid addition salt thereof.

2. A method of inhibiting blood platelet aggregation in a human in need thereof, which comprises administering to said human of an effective blood platelet aggregation inhibition amount of a compound 2-(2-methoxy-4-methylsulphinylphenyl)-1H-imidazo[4,5-c]pyridine, a pharmacologically acceptable acid addition salt thereof, or an N-oxide of said compound or said salt.

* * * * *